United States Patent [19]
Parikh et al.

[11] Patent Number: 6,096,927
[45] Date of Patent: Aug. 1, 2000

[54] PROCESS FOR REMOVAL AND RECOVERY OF AN ARYLAMINE COMPOUND

[75] Inventors: Satish R. Parikh, Rochester; Edward J. Radigan, Jr., Caledonia; Anthony M. Horgan, Pittsford; John A. Bergfjord, Sr., Macedon, all of N.Y.

[73] Assignee: Xerox Corporation, Stamford, Conn.

[21] Appl. No.: 09/365,486

[22] Filed: Aug. 2, 1999

[51] Int. Cl.$^7$ .................................................. C07C 211/00
[52] U.S. Cl. ............................................................. 564/434
[58] Field of Search ............................................ 564/434

[56] References Cited

U.S. PATENT DOCUMENTS 4,265,990  5/1981  Stolka et al. .
4,306,008  12/1981  Pai et al. .

FOREIGN PATENT DOCUMENTS 11084694  3/1999  Japan .
11228508  8/1999  Japan .

*Primary Examiner*—Paul J. Killos

[57] ABSTRACT

A process for recovery of N,N'-bis(alkylphenyl)-[1,1'-biphenyl]-4,4'-diamine from an electrophotographic imaging member, the process including providing an electrophotographic imaging member including at least one imaging layer, the imaging layer including a film forming binder and N,N'-bis(alkylphenyl)[1,1'-biphenyl]-4,4'-diamine, contacting the at least one imaging layer with warm toluene to dissolve toluene soluble materials including the film forming binder and N,N'-bis(alkylphenyl)-[1,1'-biphenyl]-4,4'-diamine to form a mixture containing undissolved material and a solution of toluene and the toluene soluble materials, isolating the solution from the undissolved material, concentrating the solution in a partial vacuum and with applied heat, cooling the concentrate, mixing the concentrate with acetone to precipitate the N,N'-bis(alkylphenyl)-[1,1'-biphenyl]-4,4'-diamine, separating the N,N'-bis(alkylphenyl)-[1,1'-biphenyl]-4,4'-diamine precipitate from the concentrate, washing the N,N'-bis(alkylphenyl)-[1,1'-biphenyl]-4,4'-diamine precipitate with acetone, drying the N,N'-bis(alkylphenyl)-[1,1'-biphenyl]-4,4'-diamine precipitate, and purifying the N,N'-bis(alkylphenyl)-[1,1'-biphenyl]-4,4'-diamine precipitate.

9 Claims, No Drawings

PROCESS FOR REMOVAL AND RECOVERY OF AN ARYLAMINE COMPOUND

BACKGROUND OF THE INVENTION

This invention relates in general to a recovery process and, more specifically, to a process for removal and recovery of an arylamine compound.

INFORMATION DISCLOSURE STATEMENT

Electrophotographic imaging members are well known and include photosensitive members (photoreceptors) commonly utilized in electrophotographic (xerographic) processes in either a flexible belt or a rigid drum configuration.

These electrophotographic imaging members comprise a photoconductive layer comprising a single layer or composite layers. One type of composite photoconductive layer used in xerography is illustrated in U.S. Pat. No. 4,265,990 which describes a photosensitive member having at least two electrically operative layers. One layer comprises a photoconductive layer which is capable of photogenerating holes and injecting the photogenerated holes into a contiguous charge transport layer. Generally, the two electrically operative layers are supported on a conductive layer with the photoconductive layer capable of photogenerating holes and injecting photogenerated holes sandwiched between the contiguous charge transport layer and the supporting conductive layer. Photosensitive members having at least two electrically operative layers, as disclosed above, provide excellent electrostatic latent images when charged with a uniform negative electrostatic charge, exposed to a light image and thereafter developed with finely divided electroscopic marking particles. The resulting toner image is usually transferred to a suitable receiving member such as paper.

One type of multilayered photoreceptor that has been employed as a belt in electrophotographic imaging systems comprises a substrate, a conductive layer, a blacking layer, an adhesive layer, a charge generating layer, a charge transport layer and a conductive ground strip layer adjacent to one edge of the imaging layers. This photoreceptor may also comprise additional layers such as an anticurl back coating and an optional overcoating layer.

As the popularity of electrophotographic systems has grown, the volume of spent photoreceptors, scrapped photoreceptors that failed to meet high quality standards and other unusable photoreceptors has also grown. Thus, the sources for these unusable photoreceptors may be from old machines, rejects from the manufacturing process, or defective or damaged photoreceptors discovered during various inspection cycles. Rejected photoreceptors may contain simple cosmetic blemishes, scratches, unacceptable electrical properties, and the like. For environmental and economic reasons, recovery and reuse of photoreceptor component materials is highly desirable while the photoreceptors are readily accessible. Once the photoreceptors are disposed of in waste disposal sites such as landfills, they pollute our land and valuable components thereof are irretrievably lost. Synthesis of new replacement material consumes valuable material resources and energy.

Since a photoreceptor can comprise as many as seven different layers, attempts at recovery and recycling of important components have failed because reuse of the recovered components did not satisfy stringent photoreceptor electrical tolerances. Although the photoreceptor material may be burned to produce heat energy, such burning can produce materials which escape through exhaust stacks and leave an ash that requires disposal.

BRIEF SUMMARY OF THE INVENTION

It is, therefore, an object of the present invention to provide an improved process for recovering components of photoreceptors.

It is another object of the present invention to provide an improved process for recovering an arylamine compound from a photoreceptor.

It is still another object of the present invention to provide an improved process for recovering an arylamine compound having excellent electrical properties.

It is yet another object of the present invention to provide an improved process for realizing economic benefits by recovering and reusing.

The foregoing objects and others are accomplished in accordance with this invention by providing a process for recovery of N,N'-bis(alkylphenyl)-[1,1'-biphenyl]-4,4'-diamine from an electrophotographic imaging member, the process comprising providing an electrophotographic imaging member comprising at least one imaging layer, the imaging layer comprising a film forming binder and N,N'-bis(alkylphenyl)[1,1'-biphenyl]-4,4'-diamine, contacting the at least one imaging layer with warm toluene to dissolve toluene soluble materials including the film forming binder and N,N'-bis(alkylphenyl)-[1,1'-biphenyl]-4,4'-diamine to form a mixture containing undissolved material and a solution of toluene and the toluene soluble materials, isolating the solution from the undissolved material, concentrating the solution in a partial vacuum and with applied heat, cooling the concentrate, mixing the concentrate with acetone to precipitate the N,N'-bis(alkylphenyl)-[1,1'-biphenyl]-4,4'-diamine to form a concentrate mixture, separating the N,N'-bis(alkylphenyl)-[1,1'-biphenyl]-4,4'-diamine precipitate from the concentrate mixture, washing the N,N'-bis(alkylphenyl)-[1,1'-biphenyl]-4,4'-diamine precipitate with acetone, drying the N,N'-bis(alkylphenyl)-[1,1'-biphenyl]-4,4'-diamine precipitate, and purifying the N,N'-bis(alkylphenyl)-[1,1'-biphenyl]-4,4'-diamine precipitate.

Generally, the imaging member treated with the process of this invention comprises a flexible supporting substrate having an electrically conductive surface and at least one imaging layer. The imaging layer may be a single layer combining the charge generating and charge transporting functions or these functions may be separated, each in its own optimized layer. The flexible supporting substrate layer having an electrically conductive surface may comprise any suitable flexible web or sheet comprising, for example, a solid thermoplastic polymer. The flexible supporting substrate layer having an electrically conductive surface may be opaque or substantially transparent and may comprise numerous suitable materials having the required mechanical properties. For example, it may comprise an underlying flexible insulating support layer coated with a flexible electrically conductive layer, or merely a flexible conductive layer having sufficient mechanical strength to support the electrophotoconductive layer or layers. The flexible electrically conductive layer, which may comprise the entire supporting substrate or merely be present as a coating on an underlying flexible web member, may comprise any suitable electrically conductive material including, for example, aluminum, titanium, nickel, chromium, brass, gold, stainless steel, copper, iodide, carbon black, graphite and the like dispersed in the solid thermoplastic polymer. The flexible conductive layer may vary in thickness over substantially wide ranges depending on the desired use of the electrophotoconductive member. Accordingly, the conductive layer can generally range in thicknesses of from about 50 Angstrom units to about 150 micrometers. When a highly flexible photoresponsive imaging device is desired, the thickness of the conductive layer may be between about 100 Angstrom units to about 750 Angstrom units. Any suitable underlying flexible support layer of any suitable material containing a thermoplastic film forming polymer alone or a thermoplastic film forming polymers in combination with other materials may be used. Typical underlying flexible support layers comprising film forming polymers include, for example, polyethylene terepthalate, polyimide, polysulfone, polyethylene naphthalate, polypropylene, nylon, polyester, polycarbonate, polyvinyl fluoride, polystyrene and the like. Specific examples of supporting substrates included polyethersulfone (Stabar S-100, available from ICI), polyvinyl fluoride (Tedlar, available from E.I. DuPont de Nemours & Company), polybisphenol-A polycarbonate (Makrofol, available from Mobay Chemical Company) and amorphous polyethylene terephthalate (Melinar, available from ICI Americas, Inc.).

The coated or uncoated flexible supporting substrate layer is highly flexible and may have any number of different configurations such as, for example, a sheet, a scroll, an endless flexible belt, and the like. Preferably, the insulating web is in the form of an endless flexible belt and comprises a commercially available biaxially oriented polyethylene terephthalate substrate known as Melinex 442, available from ICI.

If desired, any suitable charge blocking layer may be interposed between the conductive layer and the photogenerating layer. Some materials can form a layer which functions as both an adhesive layer and charge blocking layer. Typical blocking layers include polyvinylbutyral, organosilanes, epoxy resins, polyesters, polyamides, polyurethanes, silicones and the like. The polyvinylbutyral, epoxy resins, polyesters, polyamides, and polyurethanes can also serve as an adhesive layer. Adhesive and charge blocking layers preferably have a dry thickness between about 20 Angstroms and about 2,000 Angstroms.

The silane reaction product described in U.S. Pat. No. 4,464,450 is particularly preferred as a blocking layer material because it extends cyclic stability. The entire disclosure of U.S. Pat. No. 4,464,450 is incorporated herein by reference. Typical hydrolyzable silanes include 3-aminopropyltriethoxysilane, N-aminoethyl-3-aminopropyltrimethoxysilane, N-2-aminoethyl-3-aminopropyltrimethoxysilane, N-2-aminoethyl-3-aminopropyltris(ethylethoxy) silane, paminophenyl trimethoxysilane, 3-aminopropyidiethylmethylsilane, (N,N'-dimethyl 3-amino) propyltriethoxysilane, 3-aminopropylmethyidiethoxysilane, 3-aminopropyl trimethoxysilane, N-methylaminopropyltriethoxysilane, methyl[2-(3-trimethoxysilylpropylam ino)ethylam ino]3-proprionate, (N,N'-dimethyl 3-amino)propyl triethoxylilane, N,N-dimethylaminophenyltriethoxy silane, trimethoxysilylpropyldiethylenetriamine, and the like and mixtures thereof.

Generally, satisfactory results may be achieved when the reaction product of a hydrolyzed silane and metal oxide layer forms a blocking layer having a thickness between about 20 Angstroms and about 2,000 Angstroms.

In some cases, intermediate layers between the blocking layer and the adjacent charge generating or photogenerating layer may be desired to improve adhesion or to act as an electrical barrier layer. If such layers are utilized, they preferably have a dry thickness between about 0.01 micrometer and about 5 micrometers. Typical adhesive layers include film forming polymers such as polyester, polyvinylbutyral, polyvinylpyrolidone, polyurethane, polymethyl methacrylate and the like.

Electrophotographic imaging members comprise at least one imaging layer. Single imaging layers comprise photoconductive material, charge transport material and a film forming binder. Multiple imaging layers usually comprise a charge generating layer comprising a charge generating material and a charge transport layer comprising a charge transport material.

Typically, a preferred electrophotoconductive imaging member comprises a supporting substrate layer, a metallic conductive layer, a charge blocking layer, an optional adhesive layer, a charge generator layer, a charge transport layer. The electrophotoconductive imaging member may optionally have anticurl layer on the side of the substrate layer opposite the electrically active charge generator and charge transport layers. The thickness of the anticurl back coating is selected to counter balance the stress of the electrically active coating. This stress balance maintains web or belt flatness. Any suitable charge generating or photogenerating material may be employed as one of the two electrically operative layers in the multilayer photoconductor embodiment. Typical charge generating materials include metal free phthalocyanine described in U.S. Pat. No. 3,357,989, metal phthalocyanines such as copper phthalocyanine, benzimidazole perylene, quinacridones available from DuPont under the tradename Monastral Red, Monastral Violet and Monastral Red Y, substituted 2,4-diamino-triazines disclosed in U.S. Pat. No. 3,442,781, and polynuclear aromatic quinones available from Allied Chemical Corporation under the tradename Indofast Double Scarlet, Indofast Violet Lake B, Indofast Brilliant Scarlet and Indofast Orange. Other examples of charge generator layers are disclosed in U.S. Pat. No. 4,265,990, U.S. Pat. No. 4,233,384, U.S. Pat. No. 4,471,041, U.S. Pat. No. 4,489,143, 4,4507,480, U.S. Pat. No. 4,306,008, 4,299,897, U.S. Pat. No. 4,232,102, U.S. Pat. No. 4,233,383, U.S. Pat. No. 4,415,639 and U.S. Pat. No. 4,439,507. The disclosure of these patents are incorporated herein by reference in their entirety. Still other typical photoconductive layers include amorphous or alloys of selenium such as selenium-arsenic, selenium-tellurium-arsenic, selenium-tellurium, and the like.

Any suitable inactive resin binder material may be employed in the charge generator layer. Typical organic resinous binders include polycarbonates, acrylate polymers, vinyl polymers, cellulose polymers, polyesters, polysiloxanes, polyamides, polyurethanes, epoxies, and the like. Many organic resinous binders are disclosed, for example, in U.S. Pat. No. 3,121,006 and U.S. Pat. No. 4,439,507, the entire disclosures of which are incorporated herein by reference. Organic resinous polymers may be block, random or alternating copolymers. The photogenerating composition or pigment is present in the resinous binder composition in various amounts. When using an electrically inactive or insulating resin, it is important that there be particle-to-particle contact between the photoconductive particles. This necessitates that the photoconductive material be present in an amount of at least about 15 percent by volume of the binder layer with no limit on the maximum amount of photoconductive material present in the binder layer. If the matrix or binder comprises an active material, e.g. poly (N-vinyl carbazole), a photoconductive material need only comprise about 1 percent or less by volume of the binder layer with no limitation on the maximum amount of photoconductor in the binder layer. Generally for generator layers containing an electrically active matrix or binder such as poly(N-vinyl carbazole) or poly(hydroxyether), preferably from about 5 percent by volume to about 60 percent by volume of the photogenerating pigment is dispersed in about 95 percent by volume to about 40 percent by volume of binder, and preferably from about 7 percent to about 30 percent by volume of the photogenerating pigment is dispersed in from about 93 percent by volume to about 70 percent by volume of the binder. The specific proportions selected also depends to some extent on the thickness of the generator layer.

The thickness of the photogenerating binder layer is not particularly critical. Layer thicknesses from about 0.05 micrometer to about 40 micrometers have been found to be satisfactory. The photogenerating binder layer containing photoconductive compositions and/or pigments, and the resinous binder material preferably ranges in thickness of from about 0.1 micrometer to about 5 micrometers, and has an optimum thickness of from about 0.3 micrometer for best light absorption and improved dark decay stability and mechanical properties.

The relatively thick active charge transport layer, in general, comprises a film forming binder containing a dissolved or molecularly dispersed charge transporting aromatic amine. Preferably, the charge transporting aromatic amine is a N,N'-bis(alkylphenyl)-[1,1'-biphenyl]-4,4'-diamine small molecule transport material. The alkyl group in this small molecule transport material is selected from the group consisting of methyl, ethyl, propyl and n-butyl. Optimum results are achieved when the charge transporting aromatic amine is N,N'-diphenyl-N,N'-bis(3-methyl-phenyl)-(1,1' biphenyl)-4,4'-diamine dissolved or molecularly dispersed in a film forming binder. The film forming binder alone is incapable of supporting the injection of photogenerated holes from the generation material and incapable of allowing transport of holes there through. However, the addition of hole transporting N,N'-bis(alkylphenyl)-[1, 1'-biphenyl]-4,4'-diamine materials to the film forming binder polymeric materials forms a composition that is electrically active, that is, capable of supporting the injection of photogenerated holes from the generation material and capable of allowing the transport of these holes through the active layer to discharge the surface on the active layer. Thus, the charge transport layer should be capable of supporting the injection of photo-generated holes or electrons from the charge transport layer and allowing the transport of these holes or electrons through the charge transport layer to selectively discharge the surface charge. The term "dissolved" as employed herein is defined as forming a solution in which the transporting materials are dissolved in the film forming binder to form a homogeneous phase. The expression "molecularly dispersed" as used herein is defined as the charge transporting materials dispersed in the film forming binder, the charge transporting materials being dispersed in the polymer on a molecular scale. The expression "charge transporting materials" is defined herein as a material that allows the free charge photogenerated in the generator layer and injected into the transport layer to be transported across the transport layer. The active charge transport layer not only serves to transport holes or electrons, but also protects the photoconductive layer from abrasion or chemical attack and therefore extends the operating life of the photoreceptor imaging member. The charge transport layer should exhibit negligible, if any, discharge when exposed to a wavelength of light useful in electrophotography. Therefore, the charge transport layer is substantially transparent to radiation in a region in which the photoconductor is to be used. Thus, the active charge transport layer is a substantially non-photoconductive material which supports the injection of photogenerated holes or electrons from the generation layer. The active transport layer is normally transparent when exposure is effected through the active layer to ensure that most of the incident radiation is utilized by the underlying charge carrier generator layer for efficient photogeneration. When used with a transparent substrate, imagewise exposure may be accomplished through the substrate with all light passing through the substrate. In this case, the active transport material need not be absorbing in the wavelength region of use. The charge transport layer in conjunction with the charge generation layer in the instant invention is a material which is an insulator to the extent that an electrostatic charge placed on the transport layer is not conductive in the absence of illumination, i.e. a rate sufficient to prevent the formation and retention of an electrostatic latent image thereon.

Any suitable inactive resin binder soluble in the charge transport layer coating composition solvents may be employed to fabricate the transport layer. Typical inactive resin binders soluble in solvents include, for example, polycarbonate resin, polystyrene resins, polyether carbonate resins, polyester resins, copolyester resins, terpolyester resins, polystyrene resins, polyarylate resins and the like and mixtures thereof. Preferred polycarbonate resins include, for example, poly(4,4'-isopropylidenediphenyl carbonate) [polycarbonate A]; polyether carbonate resins; 4,4'-cyclohexylidene diphenyl polycarbonate [polycarbonate Z]; poly(4,4'-isopropylidene-3,3'-dimethyl-diphenyl-carbonate) [polycarbonate P]; and the like. Weight average molecular weights can vary from about 20,000 to about 1,500,000.

The preferred electrically inactive resin materials are polycarbonate resins have a weight average molecular weight from about 20,000 to about 100,000, more preferably from about 50,000 to about 100,000. The materials most preferred as the electrically inactive resin material is poly (4,4'-isopropylidene-diphenylene carbonate) with a molecular weight of from about 35,000 to about 40,000 (available as Lexan 145 from General Electric Company); poly (4,4'-isopropylidene-diphenylene carbonate) with a molecular weight of from about 40,000 to about 45,000 (available as Lexan 141 from General Electric Company); a polycarbonate resin having a molecular weight of from about 50,000 to about 100,000, (available as Makrolon from Farbenfabricken Bayer A.G.) and a polycarbonate resin having a molecular weight of from about 20,000 to about 50,000 (available as Merlon from Mobay Chemical Company). The most preferred polycarbonates resins are polycarbonate A, polycarbonate C and polycarbonate Z. Preferably, the charge transport layer comprises between about 70 percent and about 40 percent by weight of the film forming binder, based on the total weight of the dried transport layer and between about 30 percent and about 60 percent by weight of the charge transporting aromatic amine, based on the total weight of the dried transport layer.

Any suitable and conventional technique may be utilized to mix and thereafter apply the charge transport layer coating mixture to the charge generating layer. Typical application techniques include spraying, dip coating, roll coating, wire wound rod coating, and the like. Drying of the deposited coating may be effected by any suitable conventional technique such as oven drying, infra red radiation drying, air drying and the like. Generally, the thickness of the transport layer is between about 5 micrometers and about 100 micrometers, but thicknesses outside this range can also be used where suitable.

The charge transport layer should be an insulator to the extent that the electrostatic charge placed on the charge transport layer is not conducted in the absence of illumination at a rate sufficient to prevent formation and retention of an electrostatic latent image thereon. In general, the ratio of the thickness of the charge transport layer to the charge generator layer is preferably maintained between about 2:1 to 200:1 and in some instances as great as 400:1.

Anticurl backing layers are conventionally applied to the backside of the substrate layer, i.e. the side of the substrate opposite the side carrying the charge generating layer and charge transport layer. Generally, an anticurl backing layer is relatively thick, e.g. between about 10 micrometers and about 30 micrometers, depending on the thickness of the transport layer, whereas other optional coatings are much thinner such as between about 0 micrometers and about 5 micrometers.

Optionally, a thin overcoat layer may be utilized to improve resistance to abrasion. These overcoating layers may comprise organic polymers or inorganic polymers that are electrically insulating or slightly semi-conductive.

Thus, the process of this invention includes providing an electrophotographic imaging member comprising at least one imaging layer, the imaging layer comprising a film forming binder and N,N'-bis(alkylphenyl)-[1,1'-biphenyl]-4,4'-diamine.

At least one imaging layer containing N,N'-bis(alkylphenyl)-[1,1'-biphenyl]-4,4'-diamine is contacted with warm toluene to dissolve toluene soluble materials including N,N'-bis(alkylphenyl)-[1,1'-biphenyl]-4,4'-diamine to form a mixture containing a solution of toluene and the soluble materials, To promote complete contact between the toluene and the outer surface of the photoreceptor, such as a photoreceptor belt or web, the photoreceptor belt or scrap pieces thereof may be fed into a room temperature toluene bath such that all surfaces are exposed and wetted by toluene. The toluene and photoreceptor can be mixed to prevent adjacent facing or parallel surfaces from sticking together thereby blocking contact with the toluene. Optimum results are achieved when the photoreceptor is preprocessed by chopping entire belt into small pieces or by stripping off the at least one imaging layer from any underlying supporting substrate such as a flexible metalized Mylar belt. Stripping may readily be accomplished by initiating separation between the imaging layer(s) supporting substrate with a razor cut and thereafter gripping the imaging layer(s) and peeling it away from the substrate. This also leaves the flexible substrate which can be readily disposed of by burning with virtually no residue. The toluene extraction is preferably conducted at a temperature range between about 70° C. and about $105^2$C. Optimum results are achieved at a temperature between about 70° C. and about 80° C. At temperatures less than about 70° C., the solution of the N,N'-bis(alkylphenyl)-[1,1'-biphenyl]-4,4'-diamine in toluene is less effective unless very large volumes of solvent is used. A preferred solvent ratio is about 1 part N,N'-bis(alkylphenyl)-[1,1'-biphenyl]-4,4'-diamine to about 5 to about 20 parts of toluene, by volume. Optimum results are achieved with about 10 parts of heated toluene to 1 part N,N'-bis(alkylphenyl)-[1,1'-biphenyl]-4,4'-diamine. The time of contact between the photoreceptor and toluene should be long enough to ensure that most of the N,N'-bis(alkylphenyl)-[1,1'-biphenyl]-4,4'-diamine is dissolved in the toluene. The amount of time can vary depending upon the temperature, size of the photoreceptor pieces and the relative amount of toluene employed. A typical contact time is about one hour.

After toluene contact to dissolve the N,N'-bis(alkylphenyl)-[1,1'-biphenyl]-4,4'-diamine, the resulting solution of toluene liquid and dissolved components are separated from the undissolved solids. Separation may be accomplished by any suitable technique. Typical separation techniques include, for example, filtering, centrifuging, crystallization, diffusion, sublimation and the like. The solution contains the toluene liquor and dissolved N,N'-bis(alkylphenyl)-[1,1'-biphenyl]-4,4'-diamine. The remaining undissolved material after separation such as by filtering, make up the filter cake. The undissolved material will usually include, for example, metalized Mylar, polycarbonate and other insoluble material such as pigment particles. Any residual toluene in the undissolved material can removed and the undissolved material can be processed separately.

The solution of toluene and toluene soluble materials is thereafter concentrated. Any suitable technique may be employed for concentrating. Typical techniques include, for example, heating in a partial vacuum, distillation, and the like. Generally, is it desirable to remove between about 80 percent to about 90 percent by volume of toluene during the vacuum evaporation process. A temperature between about 30° C. and about 50° C. is preferred. When temperatures are less than about 30° C., the process requires an unduly long time. Temperatures of about 50° C. tend to rapidly form a thick solution that is difficult to handle. Optimum results are achieved with a temperature of about 40° C. Any suitable vacuum range may be utilized. Typical partial vacuum ranges are between about $10^{-3}$ torr and about $10^{-5}$ torr. A preferred vacuum evaporator is rotovap vacuum evaporator, e.g., model Labconco, available from Fisher Scientific. In a typical process, the solution of toluene and toluene soluble materials is vacuum rotovapped in a Labconco vessel, at an elevated temperature of about 40° C. and under a vacuum of about $10^{-4}$ torr until a thick, viscous syrup like layer enriched with N,N'-bis(alkylphenyl)-[1,1'-biphenyl]-4,4'-diamine is obtained. This thick, viscous mass contains N,N'-bis(alkylphenyl)-[1,1'-biphenyl]-4,4'-diamine, concentrated toluene and yellow impurity.

After concentrating the solution, the thick liquid concentrate is cooled. Preferably, the concentrate is cooled to a temperature of between about 10° C. and about 40° C. Optimum results are achieved when the concentrate is cooled to about 10° C.

The thick liquid concentrate is also mixed with acetone. The combination of cooling and presence of acetone causes N,N'-bis(alkylphenyl)-[1,1'-biphenyl]-4,4'-diamine to precipitate while substantially all the other materials previously dissolved in the toluene remain in solution. The proportion of toluene and acetone is adjusted to ensure that the N,N'-bis(alkylphenyl)-[1,1'-biphenyl]-4,4'-diamine precipitates out during cooling while the impurities remain in the solution. The acetone extracts substantially all of the impurities. A proportion of between about 30 and about 70 percent by volume acetone and between about 70 and about 30 percent volume of toluene is preferred. Optimum results are achieved with about 50 percent acetone and about 50 percent toluene.

After precipitation, the precipitate containing mostly N,N'-bis(alkylphenyl)-[1,1'-biphenyl]-4,4'-diamine is separated from the toluene and acetone mixture. Separation may be accomplished by any suitable technique. Typical separation techniques include, for example, filtering, centrifuging, and the like. After separation, such as by filtration, a clear toluene acetone liquid is obtained along with an off white N,N'-bis(alkylphenyl)-[1,1-biphenyl]-4,4'-diamine powder in a damp filter cake. This filter cake is washed with acetone to remove any residual impurities. The temperature during filtering is preferably between about 5° C. and about 25° C. The yield at this stage is usually about 86 to about 87 percent. Further washing of the N,N'-bis(alkylphenyl)-[1,1'-biphenyl]-4,4'-diamine filter cake with cold toluene and acetone and octane forms a product that is about 95 percent pure.

The crude N,N'-bis(alkylphenyl)-[1,1'-biphenyl]-4,4'-diamine filter cake (damp with toluene) can thereafter be dried. Vacuum drying increases the rate of drying.

The dried N,N'-bis(alkylphenyl)-[1,1'-biphenyl]-4,4'-diamine filter cake is preferably redissolved in octane. The redissolving is preferably accomplished at a temperature between about 90° C. and about 98° C. with optimum dissolution occurring at about 90° C. and about 92° C. The solution of N,N'-bis(alkylphenyl)-[1,1'-biphenyl]-4,4'-diamine and octane is thereafter purified by any suitable technique. Typical techniques include, for example, separation columns, diffusion column, and the like. A preferred purification technique utilizes a separation column such of any suitable absorbent such alumina to filter out the contaminates. For example, when the solution of N,N'-bis (alkylphenyl)-[1,1'-biphenyl]-4,4'-diamine and octane was purified by passage through an alumina separation column to remove contaminants, testing of the resulting N,N'-bis (alkylphenyl)-[1,1'-biphenyl]-4,4'-diamine by CTLC (Circular Thin Layer Chromatography) techniques, the N,N'-bis(alkylphenyl)-[1,1'-biphenyl]-4,4'-diamine was found to achieve single ring purity which is indicative of more than 99 percent pure. In a typical purification process using a 6:1 ratio alumina column with residence contact time extracted minute quantity of impurities. Since various suitable separation column adsorbents may be utilized, the time and temperature for purification may vary depending upon the adsorbent selected. After passage through the purification column, the N,N'-bis(alkylphenyl)-[1,1'-biphenyl]-4,4'-diamine typically provides a yield of about 92 percent of the material obtain after precipitation filtering of the N,N'-bis (alkylphenyl)-[1,1'-biphenyl]-4,4'-diamine in acetone. Thus, the overall yield is typically between about 72 percent and about 73 percent, based on total weight of the original N,N'-bis(alkylphenyl)-[1,1'-biphenyl]-4,4'-diamine.

Electrical evaluations performed on the recovered N,N'-bis(alkylphenyl)-[1,1'-biphenyl]-4,4'-diamine were found to match the purity of virgin starting material used for fabricating photoreceptors.

PREFERRED EMBODIMENT OF THE INVENTION

A number of examples are set forth hereinbelow and are illustrative of different compositions and conditions that can be utilized in practicing the invention. All proportions are by weight unless otherwise indicated. It will be apparent, however, that the invention can be practiced with many types of compositions and can have many different uses in accordance with the disclosure above and as pointed out hereinafter.

EXAMPLE I

An electrophotographic imaging member was provided having a thin titanium metalized layer coated on a polyester substrate (Melinex 442, available from ICI Americas, Inc.) having a thickness of 3 mils (76.2 micrometers). The metallized layer carried a thin siloxane blocking layer formed from gamma aminopropyltriethoxy silane. The siloxane layer carried a thin polyester adhesive interface layer.

The adhesive interface layer carried a photogenerating layer containing trigonal Se, particles, N,N'-diphenyl-N,N'-bis(3-methylphenyl)-1,1'-biphenyl-4,4'-diamine, and polyvinylcarbazole. This photogenerating layer had a thickness of about 2 micrometers.

The photogenerating layer carried a charge transport layer containing 50 percent by weight weight N,N'-diphenyl-N,N'-bis (3-methylphenyl)-1,1'-biphenyl-4,4'-diamine and 50 percent by weight Makrolon 5705, a polycarbonate resin commercially available from Farbensabricken Bayer A.G. The charge transport layer had a thickness of about 24 micrometers.

An anticurl coating of polycarbonate resin (Makrolon 5705, available from Bayer AG) was carried on the rear surface (side opposite the photogenerator layer and charge transport layer) of the imaging member and had a film thickness of about 14 micrometers.

EXAMPLE II

Attempts made to dissolve organic components of the various layers of a sample of the photoreceptor of Example I in toluene followed by distillation to isolate the N,N'-diphenyl-N,N'-bis (3-methylphenyl)-1,1'-biphenyl-4,4'-diamine resulted in unacceptable impurities in the final N,N'-diphenyl-N,N'-bis (3-methylphenyl)-1,1'-biphenyl-4, 4'-diamine product. These impurities caused numerous electrical problems in the final photoreceptor including high background and high dark decay.

EXAMPLE III

Samples of the photoreceptor described in Example I was chopped into small pieces and fed into a toluene bath at room temperature. All surfaces of the pieces were exposed to and wetted by the toluene. The mixture was mixed to ensure that no two adjacent facing or parallel surfaces stuck together thereby preventing contact with the toluene. After 1 hour of soaking in warm toluene at a temperature of 75° C., the toluene liquor was filtered and saved. The toluene liquor contained dissolved N,N'-diphenyl-N,N'-bis (3-methylphenyl)-1,1'-biphenyl-4,4'-diamine. The remaining filter cake contained aluminized Mylar, polycarbonate and other insoluble materials. The filter cake was saved and the toluene liquor were separately processed. The toluene liquor was concentrated by vacuum rotovapping in a Labconco, available from Fischer Scientific at 40° C. until a thick, syrup like product enriched mass containing N,N'-diphenyl-N,N'-bis (3-methylphenyl)-1,1-biphenyl-4,4'-diamine was obtained. This thick, syrup like mass contained N,N'-diphenyl-N,N'-bis (3-methylphenyl)-1,1'-biphenyl-4, 4'-diamine, concentrated toluene, and yellow impurity. The thick, syrup like mass was cooled to 20° C., and acetone, equal in volume to the toluene, was added while stirring to precipitate the N,N'-diphenyl-N,N'-bis (3-methylphenyl)-1, 1'-biphenyl-4,4'-diamine. Upon filtration of the resulting mixture a clean toluene acetone liquid was obtained along with an off-white N,N'-diphenyl-N,N'-bis (3-methylphenyl)-1,1'-biphenyl-4,4'-diamine powder in a damp filter cake. The filter cake was washed with additional acetone to purify the cake further. The crude N,N'-diphenyl-N,N'-bis (3-methylphenyl)-1,1'-biphenyl-4,4'-diamine filter cake (damp with toluene) was vacuum dried at 30° C. Yields of roughly 86–87 percent crude N,N'-diphenyl-N,N'-bis (3-methylphenyl)-1,1'-biphenyl-4,4'-diamine were obtained. This crude material was then dissolved in octane to form a solution containing 5 percent by weight N,N'-diphenyl-N, N'-bis (3-methylphenyl)-1,1'-biphenyl-4,4'-diamine. The solution was purified by passing it through an alumna column. As the solution passed through the column, all the impurities were retained by the alumina in the column and the exiting solution contained good product which was cooled to crystallize at 10° C. The product which then is washed with 10° C. in cold octane. The resulting N,N'-diphenyl-N,N'-bis (3-methylphenyl)-1,1'-biphenyl-4,4'-diamine product was tested using the CTLC (Circular Thin Layer Chromatography) method. With this testing method, the recovered N,N'-diphenyl-N,N'-bis (3-methylphenyl)1,1'-biphenyl-4,4'-diamine was found to be characterized by single ring purity which was equivalent to more than 99 percent purity. Electrical evaluation performed with the highly pure recovered product matched the performance of virgin N,N'-diphenyl-N,N'-bis (3-methylphenyl)-1,1'-biphenyl-4,4'-diamine in photoreceptors.

Although the invention has been described with reference to specific preferred embodiments, it is not intended to be limited thereto, rather those having ordinary skill in the art will recognize that variations and modifications may be made therein which are within the spirit of the invention and within the scope of the claims.

What is claimed is:

1. A process for recovery of N,N'-bis(alkylphenyl)-[1,1'-biphenyl]-4,4'-diamine from an electrophotographic imaging member, the process comprising provideing an electrophotographic imaging member comprising at least one imaging layer, the imaging layer comprising a film forming binder and N,N'-bis(alkylphenyl)[1,1'-biphenyl]-4,4'-diamine, contacting the at least one imaging layer with warm toluene to dissolve toluene soluble materials including the film forming binder and N,N'-bis(alkylphenyl)-[1, 1'-biphenyl]-4,4'-diamine to form a mixture containing undissolved material and a solution of toluene and the toluene soluble materials, isolating the solution from the undissolved material, concentrating the solution in a partial vacuum and with applied heat, cooling the concentrate, mixing the concentrate with acetone to precipitate the N,N'-bis(alkylphenyl)-[1,1'-biphenyl]-4,4'-diamine, separating the N,N'-bis(alkylphenyl)-[1,1'-biphenyl]-4,4'-diamine precipitate from the concentrate, washing the N,N'-bis(alkylphenyl)-[1,1'-biphenyl]-4,4'-diamine precipitate with acetone, drying the N,N'-bis(alkylphenyl)-[1,1'-biphenyl]-4,4'-diamine precipitate, and purifying the N,N'-bis(alkylphenyl)-[1,1'-biphenyl]-4,4'-diamine precipitate.

2. A process according to claim 1 wherein the at least one imaging layer comprises a charge generating layer and a charge transport layer.

3. A process according to claim 1 wherein the alkyl in N,N'-bis(alkylphenyl)-[1,1'-biphenyl]-4,4'-diamine is selected from the group consisting of methyl, ethyl, propyl and n-butyl.

4. A process according to claim 1 wherein the warm toluene is at a temperature of between about 70° C. and about 105° C.

5. A process according to claim 1 wherein the ratio of N,N'-bis(alkylphenyl)-[1,1'-biphenyl]-4,4'-diamine to warm toluene is between about 1 part by volume N,N'-bis (alkylphenyl)-[1,1'-biphenyl]-4,4'-diamine to about 5 to about 20 parts by volume toluene.

6. A process according to claim 1 wherein isolating of the solution from the undissolved material is accomplished by heating at a temperature of between about 30° C. and about 50° C. in partial vacuum.

7. A process according to claim 1 wherein the concentrate is cooled to a temperature of between about 10° C. and about 40° C.

8. A process according to claim 1 wherein the mixing of the concentrate with acetone is accomplished with a proportion of between about 30 and about 70 percent by volume acetone and between about 70 and about 30 percent volume of toluene.

9. A process according to claim 1 wherein purifying of the N,N'-bis(alkylphenyl)[1,1'-biphenyl]-4,4'-diamine precipitate comprises dissolving the N,N'-bis(alkylphenyl)-[1,1-biphenyl]-4,4'-diamine precipitate in octane to form a solution and passing the solution through an adsorption separation column.

* * * * *